United States Patent
Tu et al.

(10) Patent No.: US 9,891,044 B2
(45) Date of Patent: Feb. 13, 2018

(54) METHOD AND DEVICE FOR DETERMINING DEVIATION IN PRESSURE IN A BLOOD VESSEL

(71) Applicant: MEDIS ASSOCIATED B.V., Leiden (NL)

(72) Inventors: Shengxian Tu, Leiden (NL); Johan Hendrikus Christiaan Reiber, Leiden (NL); Yingguang Li, Leiden (NL)

(73) Assignee: MEDIS ASSOCIATED B.V., Leiden (NL)

( * ) Notice: Subject to any disclaimer, the term of this patent is extended or adjusted under 35 U.S.C. 154(b) by 174 days.

(21) Appl. No.: 14/661,137

(22) Filed: Mar. 18, 2015

(65) Prior Publication Data
US 2015/0268039 A1 Sep. 24, 2015

(30) Foreign Application Priority Data
Mar. 18, 2014 (NL) ..................................... 2012459

(51) Int. Cl.
*A61B 5/05* (2006.01)
*G01B 21/00* (2006.01)
(Continued)

(52) U.S. Cl.
CPC .............. *G01B 21/00* (2013.01); *A61B 5/021* (2013.01); *A61B 5/026* (2013.01);
(Continued)

(58) Field of Classification Search
CPC ......... G01B 21/00; A61B 5/489; A61B 5/107; A61B 5/021; A61B 5/02007; A61B 5/026; G01L 7/00; G01F 1/00
(Continued)

(56) References Cited

U.S. PATENT DOCUMENTS

2006/0149522 A1* 7/2006 Tang ..................... G06F 19/321
 703/11
2010/0185079 A1 7/2010 Huizenga
(Continued)

OTHER PUBLICATIONS

EuroIntervention Abstract, "Three-dimensional rendering of OCT pullbacks for assessment of side-branch ostia," *EAPCI* (2013).
(Continued)

*Primary Examiner* — Sanjay Cattungal
(74) *Attorney, Agent, or Firm* — Barnes & Thornburg LLP; Mark J. Nahnsen (57) ABSTRACT

Deviations of blood pressure due to stenosis caused by plaque pose a health risk. The deviation, often expressed in a fractional flow reserve, may be calculated on a per-location basis using deviations of the local cross-sectional area or local diameter from a reference value representing a healthy vessel. The reference value may be obtained by means of linear or higher order interpolation or linear regression techniques. Together with the flow velocity of a fluid through the vessel, a value of local deviation of a vessel geometry compared to a reference value allows for accurate, fast and efficient calculation of the fractional flow reserve for every location of the vessel for which geometry data is available. The reference value as well as actual data obtained by measurements may be represented or approximated by functions, allowing accurate and efficient calculation of data over a continuous region of the segment under scrutiny.

18 Claims, 4 Drawing Sheets

(51) Int. Cl.
*G01L 7/00* (2006.01)
*G01F 1/00* (2006.01)
*A61B 5/02* (2006.01)
*A61B 5/026* (2006.01)
*A61B 5/021* (2006.01)
*A61B 5/107* (2006.01)
*A61B 5/00* (2006.01)

(52) U.S. Cl.
CPC .......... *A61B 5/02007* (2013.01); *A61B 5/107* (2013.01); *A61B 5/489* (2013.01); *G01F 1/00* (2013.01); *G01L 7/00* (2013.01)

(58) Field of Classification Search
USPC .................................................. 600/407–480
See application file for complete search history.

(56) References Cited

U.S. PATENT DOCUMENTS

| | | | |
|---|---|---|---|
| 2011/0178383 A1 | 7/2011 | Kassab | |
| 2011/0240852 A1 | 10/2011 | Tanner | |
| 2011/0295579 A1* | 12/2011 | Tang | A61B 6/466 703/9 |
| 2012/0083696 A1 | 4/2012 | Kitamura | |
| 2012/0084064 A1* | 4/2012 | Dzenis | G06F 19/3437 703/11 |
| 2012/0130243 A1 | 5/2012 | Balocco et al. | |
| 2012/0296214 A1 | 11/2012 | Urabe | |
| 2013/0028494 A1* | 1/2013 | Groth | G06T 7/0012 382/130 |
| 2013/0090555 A1 | 4/2013 | Kassab | |
| 2014/0029821 A1 | 1/2014 | Lee | |
| 2014/0257087 A1 | 9/2014 | Elbasiony | |
| 2015/0238121 A1 | 8/2015 | Tu et al. | |
| 2015/0245776 A1 | 9/2015 | Hirohata | |
| 2015/0356734 A1 | 12/2015 | Ooga | |

OTHER PUBLICATIONS

Hahn et al., "Comparison of vessel geometry in bifurcation between normal and diseased segments: Intravascular ultrasound analysis," *Atherosclerosis*, 201: 326-331 (2008).

Medis Specials, "QAnglo® OCT Research Edition v1.0," (2012).

Pyxaras et al., "Optimization of Tryton Dedicated Coronary Bifurcation System with Coregistration of Optical Coherence Tomography and Fractional Flow Reserve," *JACC Cardio. Interventions*, 6(7): e39-40 (2013).

Wang et al., "Computerized Medical Imaging and Graphics," *Elsevier*, 38: 113-122 (2014).

\* cited by examiner

METHOD AND DEVICE FOR DETERMINING DEVIATION IN PRESSURE IN A BLOOD VESSEL

CROSS REFERENCE TO RELATED APPLICATIONS

This application claims priority to Netherlands patent application no. 2012459, filed 18 Mar. 2014. The disclosure set forth in the referenced application is incorporated herein by reference in its entirety.

TECHNICAL FIELD

The various aspects relate to determination and visualisation of pressure deviations in a blood vessel due to variation of geometrical parameters of the blood vessel.

BACKGROUND

Stenosis due to plaque in coronary vessels pose a threat to the health of a person as it hampers blood flow in the cardiovascular system of the person. Fractional flow reserve, a ratio of a first fluid pressure at a first point in a coronary artery divided by a second pressure at a second point in the coronary artery, upstream of the first point is accepted as a measure of the impact of stenosis on blood circulation in a vessel.

Blood pressures may be determined by means of intervention in the blood vessel under scrutiny with a pressure sensor. Such intervention involves a significant amount of work and poses a risk to the person under scrutiny as the vessel wall may be damaged by the pressure sensor. Methods of determining geometry of a cardiovascular system are available, like three dimensional or two dimensional quantitative coronary angiography—QCA. The output of such methods is used for elaborate numerical analysis of the vessel under scrutiny, for example by solving the complex fluid equations using computational fluid dynamics as proposed in a paper "Virtual Fractional Flow Reserve From Coronary Angiography: Modelling the Significance of Coronary Lesions, published in JACC: Cardiovascular Interventions. Such approach requires a significant amount of processing power.

Other approaches propose to treat a narrowing in a coronary artery as having a specific length and a fixed width, as presented in the paper Calculation the Translesional Pressure Gradients on Coronary Stenosis by Combining Three-dimensional Coronary Angiography Parameters with Frame Count Data, published in Computing in Cardiology. In particular the assumption of a fixed area of the narrowing reduces accuracy of the outcome of the calculations. In addition, it is subjective and not reliable to determine the length of the narrowing in practice, especially in patients with diffused and multiple coronary lesions.

SUMMARY

It is preferred to provide a more efficient method of determining deviation in pressure in a blood vessel due to variations in geometry in the blood vessel and a device for executing such method.

A first aspect provides a method of determining a pressure drop in a segment of a blood vessel. The method comprises receiving geometry data on a geometry of the segment, the segment having a proximal segment end and a distal segment end. The geometry data comprises a first geometrical parameter indicative of a first area of a first cross-section of the blood vessel at the proximal segment end; a second geometrical parameter indicative of a second area of a first cross-section of the blood vessel at the distal segment end and a third geometrical parameter indicative of a third area of a third cross-section of the blood vessel at a first location in the segment between the proximal segment end and the distal segment end. The method further comprises receiving data indicative of a fluid flow velocity of a fluid flow through the segment. Based on the first geometrical parameter, the second geometrical parameter, the third geometrical parameter and location data related to the first location, a reference geometrical parameter value at the first location is determined and based on the reference geometrical parameter value at the first location, the third geometrical parameter and the fluid flow velocity, a pressure deviation between a first fluid pressure at the proximal segment end and a second fluid pressure at the first location are determined.

By using local data, rather than data over a longer interval, accuracy can be improved. Furthermore, no complex calculations are required and the pressure deviation may be calculated at the actual point of interest, the first location.

An embodiment of the first aspect comprises, based on the third geometrical parameter and the reference geometrical parameter value at the first location, determining a geometrical parameter difference between an actual geometrical parameter at the first location based on the third geometrical parameter and the reference geometrical parameter value at the first location; wherein determining the pressure deviation between the first fluid pressure and the second fluid pressure is also based on the geometrical parameter difference.

By using the difference between actually obtained data, like diameter or area, and a reference value for diameter or area, only deviations from the reference diameter or reference area are taken into account.

A second aspect provides a computer programme product comprising computer executable code that, when loaded in a processing module of a computer, cause the computer to execute the method according to the first aspect.

A third aspect provides an arrangement for determining a pressure drop in a segment of a blood vessel. The arrangement comprises an input module arranged to receive geometry data on a geometry of the segment, the segment having a proximal segment end and a distal segment end, wherein the geometry data comprises a first geometrical parameter indicative of a first area of a first cross-section of the blood vessel at the proximal segment end, a second geometrical parameter indicative of a second area of a first cross-section of the blood vessel at the distal segment end and a third geometrical parameter indicative of a third area of a third cross-section of the blood vessel at a first location in the segment between the proximal segment end and the distal segment end; and arranged to receive a fluid flow velocity of a fluid flow through the segment. The arrangement further comprises a processing module arranged to be based on the first geometrical parameter, the second geometrical parameter, the third geometrical parameter and location data related to the first location, determine a reference geometrical parameter value at the first location; and based on the reference geometrical parameter value and the fluid flow velocity, determine a pressure deviation between a first fluid pressure at the proximal segment end and a second fluid pressure at the first location. The arrangement also comprises an output module for providing the ratio of a first fluid pressure in the segment at the first location divided by a second fluid pressure in the segment at the proximal segment end.

BRIEF DESCRIPTION OF THE DRAWINGS

The various aspects and embodiments thereof will now be further discussed in conjunction with Figures. In the Figures.

FIG. 3 A: shows a segment of a first blood vessel with stenotic regions;

FIG. 3 B: shows a difference function depicting difference between a measured area value and a reference area value;

FIG. 3 C: shows a segment of a second blood vessel with stenotic regions and a side branch; and FIG. 3 D: shows a derivative difference function depicting a derivative of the difference function.

DETAILED DESCRIPTION

Figure 1:
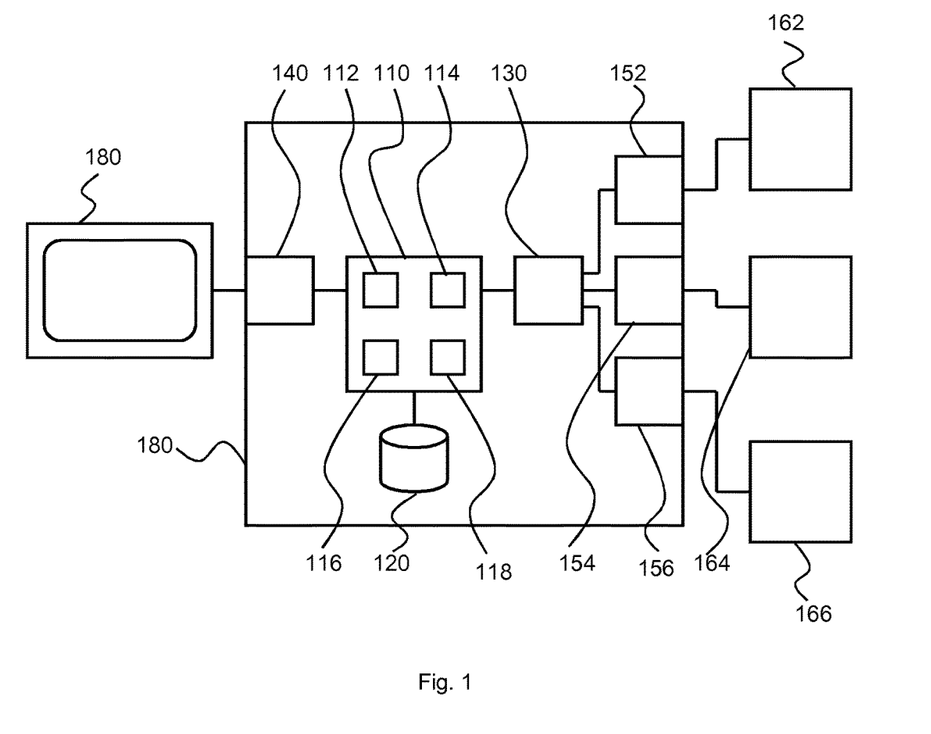
FIG. 1: shows an image data processing device.

FIG. 1 shows an image data processing device 100. The image data processing device 100 comprises a microprocessor 110 as a processing unit. The microprocessor may comprise various sub-modules for performing various steps. The sub-modules may be provided by hardwiring of the microprocessor 110 during manufacturing, after manufacturing by fusing or during use by programming of the microprocessor 110 by means of software.

The image data processing device 100 further comprises a memory module 120 for storing data to be processed, processed data and for storing computer executable code for programming the microprocessor 100 to execute the methods as discussed below. The image data processing device 100 also comprises an image rendering module 140 for rendering of data for displaying rendered data on a connected display 180 and a data input module 130 for receiving image data to be processed. The image data processing device 100 optionally comprises a first data acquisition unit 162 for receiving raw data from an X-ray imaging system, a second data acquisition unit 164 for receiving raw data from a CT imaging system and a third data acquisition unit 166 for receiving raw data from an optical coherence tomography (OCT) probe. In another embodiment, the data acquisition units are comprised by another device or by the imaging device itself.

Figure 2:
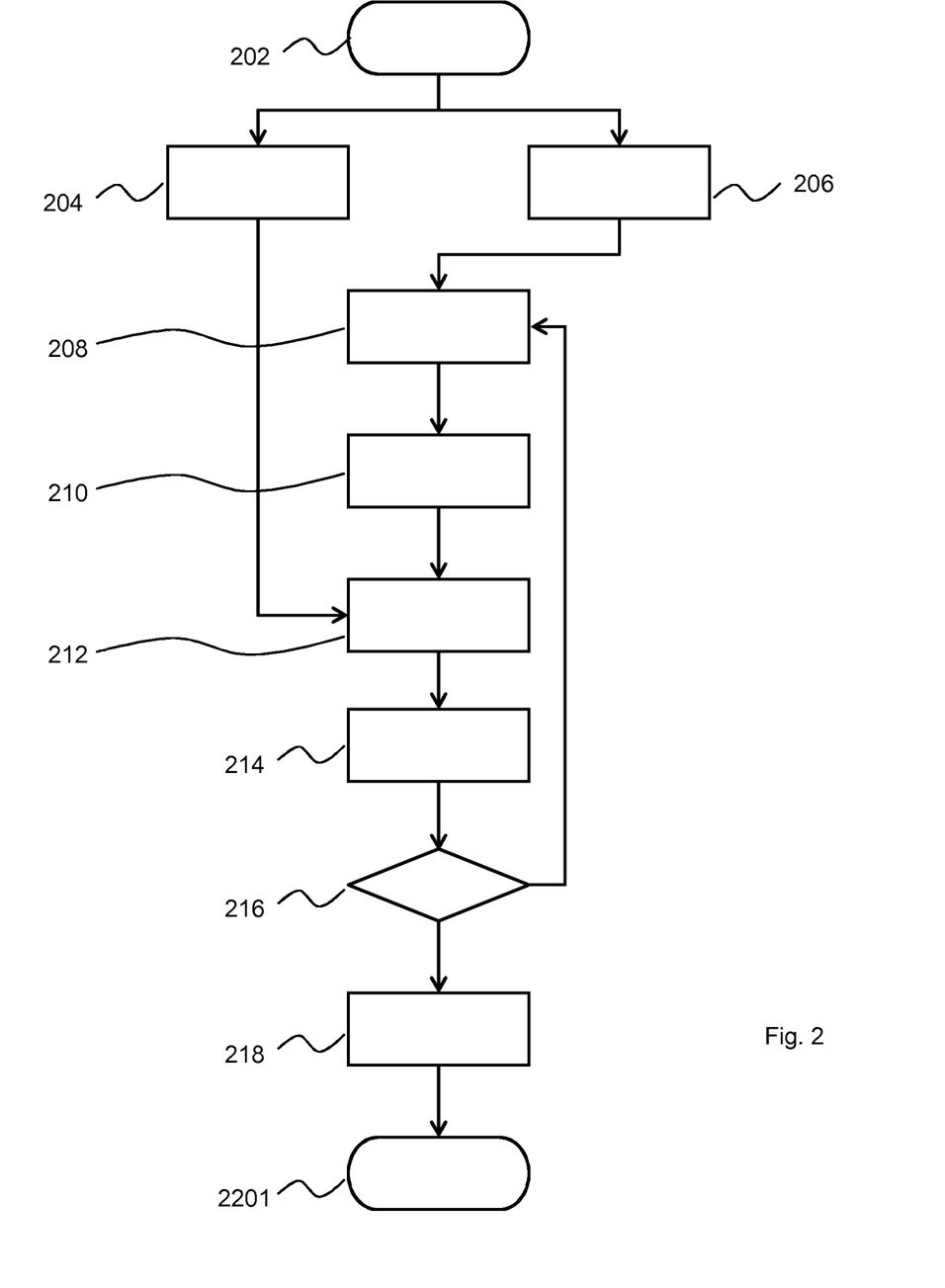
FIG. 2: shows a first flowchart.

FIG. 2 shows a flowchart 200 depicting a process executable by the image data processing device 100. Directly below, a short summary of the various steps of the process depicted by the flowchart 200 are summarised.

202 start process
204 obtain fluid flow velocity
206 obtain vessel geometry data
208 determine reference area data
210 determine difference reference area and obtained area data
212 Determine derivative of difference function
214 determine pressure drop at location
216 ready for all points?
218 display data
220 end The process starts in a terminator 202 and proceeds to step 206 by obtaining geometry data of a blood vessel. In the subsequent description, data is obtained from a coronary vascular system and the arteries in particular. Geometry data may be obtained in various ways. The data may be two-dimensional or three-dimensional.

X-ray data is obtained by means of an X-ray imaging system, using a contrast fluid inserted at the beginning of a coronary artery. Such data is two-dimensional. By obtaining images of the coronary artery system at different angles, preferably 25 degrees or more apart, a three-dimensional reconstruction of the coronary artery system may be reconstructed. If only one image is taken, two dimensional data is obtained.

Alternatively or additionally, geometry data may be obtained using X-ray computed tomography, intravascular ultrasound (IVUS), optical coherence tomography (OCT), other, or a combination thereof. IVUS and OCT do not provide information on the whole structure of a blood vessel and in particular not about any bends in the vessel, but this information is not required. The most important information to be obtained is a diameter of a blood vessel and/or a cross-sectional area of the blood vessel at multiple locations. The diameter and/or cross-sectional area is preferably determined perpendicular to a longitudinal centreline of the vessel under scrutiny.

Furthermore, a distance between the locations where geometry data is obtained and a reference location in the vessel under scrutiny or a segment thereof is determined. In most cases, a specific segment of a coronary artery system is under scrutiny. In such case, the proximal end of such segment, the upstream end of the segment, may be taken as a reference point. Alternatively, the distal end of the segment may be taken as a reference point.

If two dimensional geometry data is obtained, data on a diameter of a blood vessel may be used to determine the area of a cross section of a blood vessel using a circular approximation of the cross section of the blood vessel.

Figure 3:
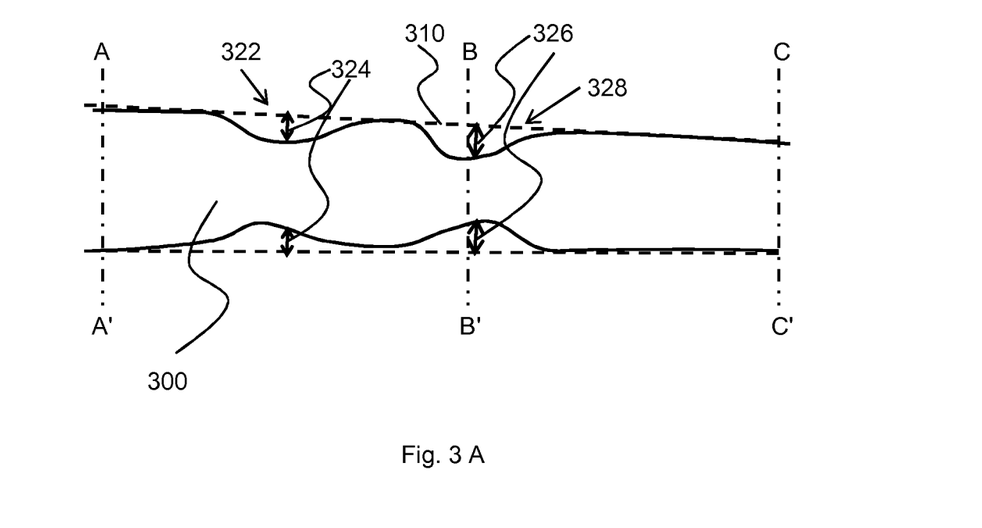

FIG. 3 A and FIG. 3 B show longitudinal cross-sections of blood vessels. FIG. 3 A shows a segment of a first blood vessel 300. In the first blood vessel 300, blood flows from a proximal end indicated by the line A-A' to a distal end indicated by a line C-C'. At the proximal and distal end of the first blood vessel 300, areas of cross-sections of the blood vessels are determined. With this information, reference area data is determined as a function of a location in the segment of the first blood vessel 300 by a reference data determining sub-module 112 of the microprocessor 110.

In this particular embodiment, the reference area is a linear function of the distance from the proximal end, which function yields at the distal end the actual value of the cross-section area at the distal end. This reference area data is determined in step 208 and indicated by a reference line 310 in FIG. 3 A. Alternatively, higher order approximations may be used instead of a linear approximation. The approximation may be provided as a single function or as a spline defined by multiple functions. The functions may be polynomials of first, second or higher order, exponential functions, periodical functions, hyperbolic functions, other, or a combination thereof.

FIG. 3 A also shows narrowings of the first blood vessel 300. FIG. 3 A shows a first stenotic section 322 and a second stenotic section 328 in the first blood vessel 300. The stenosis in the first blood vessel yield a smaller area for blood to flow through, which, in turn, results in a pressure drop in the fluid and the blood in particular. In step 210, a difference between the reference area and the actual area of the first blood vessel 300 is determined. An area difference for the first stenotic section 322 with the reference area function is indicated by arrows 324 and an area difference for the second stenotic section 328 is indicated by arrows 326.

Calculation of the difference between reference and actually measured or otherwise obtained area data may be done in a continuous way, by approximating the actual vessel inner space by means of, for example, a spline. This allows a continuous determination of a difference function, indicating a difference between the reference vessel diameter or area and the actually measured vessel diameter or area, as a function of a distance from a reference point. The proximal point A-A' may be such reference, but another reference point may be chosen as well.

Alternatively, area data of the first blood vessel 300 is available in a non-continuous way, at discrete intervals. Such may be the case if cross-section data of the first blood vessel 300 is used that is directly obtained by means of OCT, without interpolation. In such case, the difference between a reference value for the diameter or cross-section and an actually measured value is calculated per position where measured data is available. With difference data available for locations where measured data is available, a continuous approximation may be provided for the difference value as a function of a distance from a reference.

FIG. 3 B shows a difference curve 340 of a difference function indicating a difference between reference values and actually measured values for the first blood vessel 300 as depicted by FIG. 3 B. The curve 340 is a continuous function of the distance from the proximal point A-A. Alternatively, a further difference curve 340 is non-continuous but rather defined by means of discrete difference values, with one difference value defined for at least some of the locations and preferably all location for which measured data is available.

Instead of a linear determination of a reference area—or reference diameter, for that matter—, a step function may be used. This is particularly advantageous if a segment of a blood vessel under scrutiny has a side branch, within the segment under scrutiny. After the branching off, the main branch will, also in a healthy vessel, have a smaller diameter to ensure blood pressure in the main branch is substantially equal before and after the branching off. This phenomenon may be taken in to account while determining a reference area. This is depicted in FIG. 3 B.

FIG. 3 C shows a second blood vessel 350 having a side branch 380. The second blood vessel 350 has a first stenotic region 372 and a second stenotic region 362. Between the proximal end indicated by the line A-A' and the branching off of the side branch 380, a first reference area function indicated by a first reference line 362 is defined. Between the branching off of the side branch 380 and the distal end of the segment of the second blood vessel 350 under scrutiny, indicated by the line C-C', a second reference line 364 is defined. Both reference lines indicate estimations of a diameter or area of a healthy blood vessel at a particular location.

In yet another alternative, a reference diameter or reference area is provided by means of numerical approximation, like interpolation or regression techniques or by means of approximation by means of a higher-order polynomial or exponential function.

With general anatomy of the coronary artery system known, a reference area or reference diameter function may be improved by knowing in which vessel of the coronary artery system the distal position is located in.

Preferably, five types of coronary vessels are defined, being the left main trunk, the left anterior descending artery, the left circumflex artery, the right coronary artery and other side branches. The classification may be further narrowed by defining two classes; a first class with the left main trunk and the left anterior descending artery and a second class with the left circumflex artery, the right coronary artery and other side branches.

With difference data, difference between measured data and reference data or an approximation thereof by means of for example a spline or a single function, further computations may be performed yielding data for more accurate determination of pressure deviations. To this end, a derivative of a difference function is optionally derived from a difference function determined earlier in step 214. If the difference function is provided as a continuous or semi-continuous function or spline, a derivative function or derivative functions may be obtained using standard mathematical methods. Alternatively, numerical approximations may be used.

If the difference function is defined by means of discrete values, a derivative function may be defined by defining, at a first location, a ratio, like a percentage, by which the area or diameter at the first location differs from a second location preceding and preferably directly preceding the first location. FIG. 3 D shows a second curve 390 indicating a first derivative function of the difference function shown by the first curve 340 in FIG. 3 B. Alternatively or additionally, higher order derivatives may be derived in any way described above.

In step 204, data on velocity of a fluid through the vessel, like blood or a contrast fluid, is obtained. The fluid velocity within the segment of a vessel under scrutiny is preferably obtained by means of x-ray imaging while having injected a contrast fluid, using multiple frames upon and right after insertion of the contrast fluid in the blood vessel under scrutiny. By determining the length of the segment under scrutiny and the time for the contrast fluid to arrive, an average flow velocity may be determined. Optionally, multiple fluid velocities may be determined for sub-segments. The fluid flow velocity is obtained by a velocity determining sub-module 116 of the microprocessor 110. Alternatively, a fixed empirical fluid velocity, obtained by means of review of x-ray images or other image data is determined and used for further computations. In yet another alternative, a velocity obtained from within a blood vessel may be used.

With the fluid flow velocity and the area difference data—the difference between the reference area value and the actually measured data—, a deviation of pressure in a first location in the vessel compared to a second location in the vessel due to a variation of the area from the reference area may be calculated. This calculation is performed in step 212, by a pressure deviation determination sub-module 118 of the microprocessor 110. The pressure deviation is preferably determined as a fractional flow reserve. The fractional flow reserve is determined as a ratio between a pressure distal to a stenotic area and a pressure proximal to a stenotic area. The stenotic area may be of finite length or of infinitesimally small length. The latter option is particularly advantageous if the actually measured diameter or area of the blood vessel under scrutiny is approximated by a function like a spline. By means of the difference function and the flow velocity, the fractional flow reserve at a specific location may be determined. The fractional flow reserve may be determined directly from the difference function—the difference between reference and the actually measured diameter—and the fluid flow velocity.

Alternatively, the fractional flow reserve may be determined by determining a pressure drop due to stenosis in a section of the segment under scrutiny. Pressure is determined at a proximal end of a section under scrutiny. The proximal pressure can be measured by a guiding catheter that is used to the inject contrast fluid as discussed above. Or the proximal pressure may be approximated using the systolic and diastolic blood pressures of the person under scrutiny. In addition, it is also reasonable to assume there is a fixed proximal pressure since it will not change that much the computation result of the method discussed here. The pressure drop due to the stenosis, whether over a finite length of the segment of the blood vessel under scrutiny or over an infinitesimally small length, is subsequently a function of the variation of diameter or area and of the flow velocity of fluid determined earlier. With the pressure drop and the proximal blood pressure, the blood pressure distal to the stenotic area may be determined—the distal blood pressure. And with the distal blood pressure and the proximal blood pressure, the fractional flow reserve may be determined.

As indicated above, a derivative of the difference function may be taken into account for determining pressure drop at specific locations within the vessel. This provides a more accurate approximation of pressure drops, as abrupt narrowing of a blood vessel may result in a larger pressure drop than a gradual narrowing of a blood vessel. Another advantage of taking first and/or higher order derivatives into account is that lesions in a vessel do not have to be defined for further calculations. Instead, continuous data is used for determining pressure variations, where small and large deviations from reference value are taken into account.

Having determined a fractional flow reserve or another form of deviation in blood pressure over a specific section of a segment under scrutiny, the process determines whether all points of interest have been analysed and the values to be obtained have been determined in decision 216. If points to be calculated remain, the process branches back to step 208 for determining reference data for a subsequent section. After this, the process continues as discussed above. Alternatively, first all reference values—area or diameter—for the whole section are calculated. In such case, branching back is not required.

Having calculated pressure deviations at all locations of interest for the segment of the blood vessel under scrutiny, data is displayed in step 218. Data may be displayed on the display 180 in a table, but graphical presentation of data is preferred. Data may be displayed on a three-dimensional or two-dimensional representation of a coronary arterial system as obtained using a method discussed above. Locations or areas with a large pressure deviation—or a low fractional flow reserve—are preferably presented in a first colour, shade or other indication varying significantly from a second colour, shade or other indication indicating locations or areas with a small pressure deviation—or high fractional flow reserve. Having displayed the data, the process ends in a terminator 220.

In summary, the various aspects relate to calculation of a deviations of blood pressure. The deviation, often expressed in a fractional flow reserve, may be calculated on a per-location basis using deviations of the local cross-sectional area or local diameter from a reference value representing a healthy vessel. The reference value may be obtained by means of linear or higher order interpolation or linear regression techniques. Together with the flow velocity of a fluid through the vessel, a value of local deviation of a vessel geometry compared to a reference value allows for accurate, fast and efficient calculation of the fractional flow reserve for every location of the vessel for which geometry data is available. The reference value as well as actual data obtained by measurements may be represented or approximated by functions, allowing accurate and efficient calculation of data over a continuous region of the segment under scrutiny.

Expressions such as "comprise", "include", "incorporate", "contain", "is" and "have" are to be construed in a non-exclusive manner when interpreting the description and its associated claims, namely construed to allow for other items or components which are not explicitly defined also to be present. Reference to the singular is also to be construed in be a reference to the plural and vice versa.

In the description above, it will be understood that when an element such as layer, region or substrate is referred to as being "on", "onto" or "connected to" another element, the element is either directly on or connected to the other element, or intervening elements may also be present.

Furthermore, the invention may also be embodied with less components than provided in the embodiments described here, wherein one component carries out multiple functions. Just as well may the invention be embodied using more elements than depicted in the Figures, wherein functions carried out by one component in the embodiment provided are distributed over multiple components.

A person skilled in the art will readily appreciate that various parameters disclosed in the description may be modified and that various embodiments disclosed and/or claimed may be combined without departing from the scope of the invention.

It is stipulated that the reference signs in the claims do not limit the scope of the claims, but are merely inserted to enhance the legibility of the claims.

The invention claimed is:

1. Method of determining a pressure drop in a segment of a blood vessel, the method comprising:
   Receiving geometry data on a geometry of the segment, the segment having a proximal segment end and a distal segment end, the geometry data comprising:
   a first geometrical parameter indicative of a first area of a first cross-section of the blood vessel at the proximal segment end;
   a second geometrical parameter indicative of a second area of a second cross-section of the blood vessel at the distal segment end;
   a third geometrical parameter indicative of a third area of a third cross-section of the blood vessel at a first location in the segment between the proximal segment end and the distal segment end;
   Receiving data indicative of a fluid flow velocity of a fluid flow through the segment;
   Based on the first geometrical parameter, the second geometrical parameter, the third geometrical parameter and location data related to the first location, determining a reference geometrical parameter value at the first location;
   Based on the reference geometrical parameter value at the first location, the third geometrical parameter and the fluid flow velocity, determining a pressure deviation between a first fluid pressure at the proximal segment end and a second fluid pressure at the first location.

2. Method according to claim 1, further comprising, based on the third geometrical parameter and the reference geometrical parameter value at the first location, determining an geometrical parameter difference between an actual geometrical parameter at the first location based on the third geometrical parameter and the reference geometrical parameter value at the first location; wherein determining the pressure deviation between the first fluid pressure and the second fluid pressure is also based on the geometrical parameter difference.

3. Method according to claim 1, further comprising:
   Determining a reference geometrical parameter function representing reference geometrical parameter values as a function of a distance from a reference point in the segment; and
   Determining a difference function representing geometrical parameter differences between the reference geometrical parameter function and received geometry data as a function of a distance from the reference point; and Wherein determining the pressure deviation between the first fluid pressure and the second fluid pressure is based on the difference function.

4. Method according to claim 3, further comprising determining a derivative difference function as a derivative of the difference function and wherein determining the pressure deviation between the first fluid pressure and the second fluid pressure is based on the derivative difference function.

5. Method according to claim 1, wherein the pressure deviation is calculated as ratio of a first fluid pressure in the segment at the first location divided by a second fluid pressure in the segment at the proximal segment end.

6. Method according to claim 5, wherein:
Receiving geometry data further comprises receiving a fourth geometrical parameter indicative of a fourth area of a fourth cross-section of the blood vessel at a second location in the segment between the proximal segment end and the first location; and
Determining the ratio between a first fluid pressure in the segment at the proximal segment end and a second fluid pressure in the segment at the first location is also based on the fourth geometrical parameter.

7. Method according to claim 6, further comprising determining a ratio between the first fluid pressure and a third fluid pressure in the segment at the second location and wherein determining the ratio between a first fluid pressure in the segment at the proximal segment end and a second fluid pressure in the segment at the first location is also based on the ratio between the first fluid pressure and the third fluid pressure.

8. Method according to claim 1, wherein determining a reference geometrical parameter value at the first location comprises a linear normalisation as a function of a position in the segment.

9. Method according to claim 8, wherein the linear normalisation is a normalisation between the proximal end and the distal end.

10. Method according to claim 1, wherein the first location data related to the first location comprise a distance between the first location and the proximal end.

11. Method according to claim 1, wherein the fluid flow velocity is determined from the proximal segment end to the distal segment end.

12. Method according to claim 1, further comprising:
Receiving a first multitude of two-dimensional images of the blood vessel under the first angle, the images comprised by the first multitude being sequential in time and displaying a fluid in the blood vessel; and
Determining the fluid flow velocity from the first multitude of two-dimensional images.

13. Method according to claim 11, wherein the determined fluid flow velocity is an average velocity of the fluid through the segment.

14. Method according to claim 1, further comprising:
Receiving at least a first two-dimensional image of the blood vessel under a first angle;
Receiving at least a second two-dimensional image of the blood vessel under a second angle, the relative angle between the first angle and the second angle being at least 25 degrees;
Reconstructing a three-dimensional representation of the vessel system.

15. Method according to claim 1, wherein the blood vessel is a coronary artery.

16. Method according to claim 1, wherein receiving geometry data comprises obtaining the geometry data by means of quantitative coronary angiography.

17. Computer programme product comprising computer executable code that, when loaded in a processing module of a computer, causes the computer to execute the method according to claim 1.

18. Arrangement for determining a pressure drop in a segment of a blood vessel, the arrangement comprising:
An input module arranged to:
Receive geometry data on a geometry of the segment, the segment having a proximal segment end and a distal segment end, the geometry data comprising:
a first geometrical parameter indicative of a first area of a first cross-section of the blood vessel at the proximal segment end;
a second geometrical parameter indicative of a second area of a first cross-section of the blood vessel at the distal segment end;
a third geometrical parameter indicative of a third area of a third cross-section of the blood vessel at a first location in the segment between the proximal segment end and the distal segment end;
Receive a fluid flow velocity of a fluid flow through the segment;
A processing module arranged to:
Based on the first geometrical parameter, the second geometrical parameter, the third geometrical parameter and location data related to the first location, determine a reference geometrical parameter value at the first location; and
Based on the reference geometrical parameter value and the fluid flow velocity, determine a pressure deviation between a first fluid pressure at the proximal segment end and a second fluid pressure at the first location; and
An output module for providing the ratio of a first fluid pressure in the segment at the first location divided by a second fluid pressure in the segment at the proximal segment end.

* * * * *